(12) United States Patent
Lee et al.

(10) Patent No.: US 6,663,756 B2
(45) Date of Patent: Dec. 16, 2003

(54) MICROCHIP-TYPE OXYGEN GAS SENSOR BASED ON DIFFERENTIAL POTENTIOMETRY

(75) Inventors: Dong Kwon Lee, Goyang-si (KR); Tae Young Kang, Seoul (KR); Sung Hyuk Choi, Kwachun-si (KR); Jae Seon Lee, Seoul (KR); Hakhyun Nam, Seoul (KR); Geun Sig Cha, Seoul (KR)

(73) Assignee: i-Sens Inc., Seoul (KR)

( * ) Notice: Subject to any disclaimer, the term of this patent is extended or adjusted under 35 U.S.C. 154(b) by 12 days.

(21) Appl. No.: 09/982,490

(22) Filed: Oct. 18, 2001

(65) Prior Publication Data

US 2002/0070112 A1 Jun. 13, 2002

(30) Foreign Application Priority Data

Oct. 19, 2000 (KR) .......................... 2000-61669

(51) Int. Cl.⁷ ............... G01N 27/31; G01N 27/333; G01N 27/404
(52) U.S. Cl. ............... 204/415; 204/412; 204/416; 204/418; 204/419; 204/433; 204/435; 204/290.14; 204/292; 205/783; 205/787.5; 205/789
(58) Field of Search ................. 204/412, 416, 204/418, 419, 415, 435, 290.14, 292, 420, 433

(56) References Cited

U.S. PATENT DOCUMENTS 3,676,319 A * 7/1972 Kirsten
4,272,328 A * 6/1981 Kim et al.
4,797,192 A * 1/1989 Takiguchi
5,183,549 A * 2/1993 Joseph et al.

OTHER PUBLICATIONS

An article entitled "Potentiometric oxygen sensor based on mixed potential of cobalt wire electrode," By Meruva et al., published by Analytica Chimica Acta 341 (1997) month unavailable pp. 187–194.

An article entitled, "Solid-state ion sensors with a liquid junction-free polymer membrane . . . ," By Yoon et al., published by Sensors and Actuators B 64 (2000) month unavailable pp. 8–14.

An article entitled "A Planar pCO2 Sensor with Enhanced Electrochemical Properties," By Shin et al., published by Analytical Chemistry, vol. 72, No. 18, Sep. 15, 2000, pp. 4468–4473.

* cited by examiner

*Primary Examiner*—T. Tung
(74) *Attorney, Agent, or Firm*—Bachman & LaPointe, P.C.

(57) ABSTRACT

Disclosed is a microchip-based differential-type potentiometric oxygen gas sensor, which comprises a working electrode and a reference electrode. The working electrode is composed of a cobalt-plated electrode, a buffered hydrogel, and an ion sensitive gas permeable membrane while the reference electrode is composed of an oxygen non-sensitive silver chloride electrode and the same ion-selective gas-permeable membrane of working electrode. By taking advantage of the corrosion potential, the microchip-based oxygen gas sensor can accurately and quickly detect the content of dissolved oxygen in a sample solution. With this structure, the oxygen gas sensor is applied to a microchip-based all potentiometric multi-sensor capable of detecting two or more ions and gas species on a single chip.

17 Claims, 12 Drawing Sheets

US 6,663,756 B2

MICROCHIP-TYPE OXYGEN GAS SENSOR BASED ON DIFFERENTIAL POTENTIOMETRY

FIELD OF THE INVENTION

The present invention relates to a microchip-type oxygen gas sensor based on differential potentiometry. The microchip-type oxygen gas sensor according to the present invention comprises a working electrode and a reference electrode, wherein the working electrode is comprised of cobalt-plated electrode, a buffered hydrogel and ion-selective gas-permeable membrane, and the reference electrode is comprised of a Ag/AgCl electrode, which is non-sensitive to oxygen gas and an ion-selective gas-permeable membrane. The present invention also relates to a multi-sensor being capable of detecting two or more ions or gas species on a single chip.

BACKGROUND OF THE INVENTION

Oxygen gas is one of essential factors to aquatic livings and human beings, and the quantification of the content of oxygen gas is of concern in a physiological field, a industrial field and the environmental field.

Conventional techniques for the quantification of the content of oxygen gas are largely classified into two categories; an optical method and an electrochemical method.

The optical method quantitatively measures how much oxygen gas has quenched photons emitted from fluorescent or phosphorescent material. Alternatively, it measures the variance of absorption caused by the formation of the reversible bond to oxygen gas. However, the optical method has a disadvantage that it requires very expensive instruments such as light source, spectrometer, etc. As thus, an electrochemical method has been widely used.

Currently, Clark-type amperometric sensors, galvanic sensors, and solid-state electrolyte potentiometric sensors have been used in the electrochemical method. However, the Clark-type sensors and the galvanic sensors have several disadvantages, for example, difficulty in fabrication of a microchip-type sensor. Based on being stable signals, the solid-state electrolyte potentiometric sensors have been used for measuring the content of oxygen gas exhausted from automobile engines and flues. Unfortunately, none of the solid-state electrolyte potentiometric sensors that can be applied for measuring the content of oxygen gas dissolved in aqueous solution at room temperature is commercially available to date.

In the meanwhile, as an working electrode of the potentiometric sensor, an ion selective electrode is widely used for quantifying ion and gas species in field of food chemistry, fermentation process, environmental analysis as well as clinical chemistry in relation to blood dialysis, continuous and automatic measurement of blood electrolytes, and extracoporeal circulation of blood. Particularly, analysis of biomaterials in blood plays an important role in modern medical diagnosis.

Recently, chemical sensors for clinical blood analysis have been widely studied in the world. The sensors should give easy, accurate and economic analysis of a sample to be tested. Point-of-care and high sensitivity are also required for allowing health care personnel to perform analysis for themselves and with a small quantity. Further, a microchip-based disposable form and a multi sensor capable of detecting two or more ions and gas species are preferable for universal application.

SUMMARY OF THE INVENTION

Leading to the present invention, the intensive and thorough research on oxygen gas sensor, conducted by the present inventors, resulted in the finding that the content of oxygen gas dissolved in a sample solution can be quantitatively determined by measuring corrosion potential produced by the oxidation of cobalt metal and reduction of oxygen.

Therefore, it is an object of the present invention to provide a microchip-type potentiometric oxygen gas sensor capable of quantitatively measuring the content of oxygen gas dissolved in a sample solution.

It is another object of the present invention to determine the conditions under which cobalt metal is introduced to the oxygen gas sensor.

It is a further object of the present invention to provide formulations of a buffered hydrogel and an ion-selective gas-permeable membrane.

It is still a further object of the present invention to provide a microchip-based potentiometric multi-sensor capable of detecting two or more ions or gas species.

These and other objects can be addressed by providing a microchip-type potentiometric oxygen gas sensor comprising a working electrode and a reference electrode, wherein the working electrode is comprised of cobalt-plated electrode, a buffered hydrogel and ion-selective gas-permeable membrane, and the reference electrode is comprised of a Ag/AgCl electrode, which is non-sensitive to oxygen gas and an ion-selective gas-permeable membrane.

The ion-selective gas-permeable membrane in the present invention can be selected from various types of ion selective membranes, preferably hydrogen ion-selective 15 or potassium ion selective membrane 41. Along with the introduction of hydrogen ion selective membrane 15, the reference electrode further comprises a buffered hydrogel layer 14.

BRIEF DESCRIPTION OF THE DRAWINGS

FIG. 1$b$ is a schematic cross sectional view showing the structure of a potentiometric multi-sensor according to the present invention.

FIG. 3$b$ is a calibration curve for the oxygen sensitivity shown in FIG. 3$a$.

FIG. 4$b$ is a graph showing the sensitivity for potassium ion of a reference electrode (c) and a working electrode (d), each containing a potassium ion selective membrane 41.

FIG. 5$a$ is a graph showing the sensitivity and recovery time period of the differential-type oxygen gas sensor according to the change of oxygen concentration through a flow injection analysis.

FIG. 5b is a calibration curve for the oxygen sensitivity shown in FIG. 5a.

FIG. 8b is a calibration curves for each ion shown in FIG. 8a.

Figure 1A:
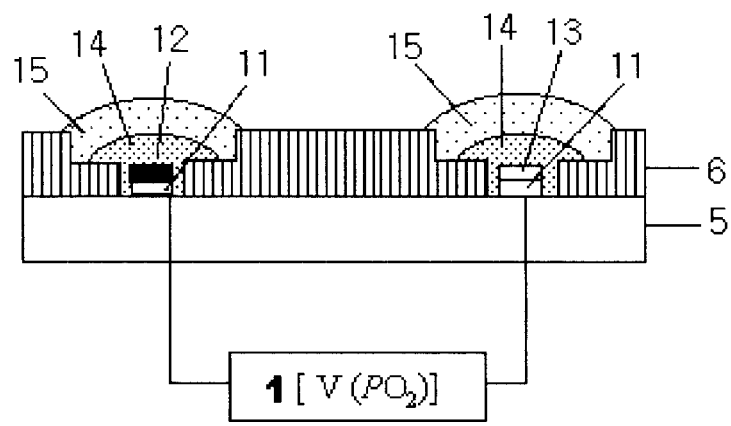
FIG. 1$a$ is a schematic cross sectional view showing the structure of a microchip-based potentiometric oxygen gas sensor according to the present invention.

1: $PO_2$ gas sensor
11: Ag—Pt electrode layer
12: Ag/AgCl electrode layer
13: Cobalt-plated electrode
14: Buffered hydrogel layer
15: Hydrogen ion selective membrane
2: pH sensor
21: Hydrogel layer
22: Aromatic PU membrane
3: $PCO_2$ gas sensor
31: Unbuffered hydrogel layer
4: pK sensor
41: Potassium ion selective membrane
5: Alumina substrate
6: Insulating film

DETAILED DESCRIPTION OF THE INVENTION

The present invention relates to a microchip-type oxygen gas sensor based on differential potentiometry comprising a working electrode and a reference electrode, wherein the working electrode is comprised of cobalt-plated electrode, a buffered hydrogel and ion-selective gas-permeable membrane, and the reference electrode is comprised of a Ag/AgCl electrode, which is non-sensitive to oxygen gas, and the same kind of ion-selective gas-permeable membrane as that of the working electrode.

The microchip-based differential-type oxygen gas sensor quickly and accurately measure the content of oxygen gas dissolved in a sample solution by potential difference between the working electrode and the reference electrode.

The principle of the microchip-type potentiometric oxygen gas sensor is explained in detail.

The oxidation of the cobalt metal and reduction of oxygen take place in the oxygen gas sensor. The reactions of the oxygen gas sensor can be summarized as follows:

Oxidation of Cobalt Metal $$2Co + 2H_2O \rightleftharpoons 2CoO + 4H^+ + 4e^-$$

Reduction of Oxygen $$O_2 + 4H^+ + 4e^- \rightleftharpoons 2H_2O$$

Corrosion Reaction of Cobalt Metal $$2Co + O_2 \rightleftharpoons 2CoO$$

Electron transfer generated during the redox reaction induces an oxidative current and a reductive current. The mixed potential (corrosion potential) of the steady state is formed when two currents reached to the same magnitude, quantitatively varies in proportional to the content of oxygen gas. Thus, the content of oxygen gas dissolved in a sample solution can be quantitatively determined by measuring the corrosion potential.

However, it was found that the sensitivity of cobalt to oxygen was greatly affected by such factors as stirring speed, ionic strength, pH of sample, buffer properties, and presence of anions. The influence of these factors on the sensitivity of cobalt to oxygen can be negated by the introduction of a buffered hydrogel and a gas permeable membrane. In this regard, formulations of the buffered hydrogel plays an important role in optimizing the sensitivity of the cobalt and shortening the hydration time, thereby enabling to quickly and accurately measure the content of dissolved oxygen gas.

In addition, the introduction of ion-selective gas-permeable membrane is advantageous in that it substantially lowers the high resistance of conventional polymeric gas-permeable membranes. In other words, the ion-selective gas-permeable membrane enables to separate a reference electrode from a working electrode.

The application of the preferred embodiments of the present invention is best understood with reference to the accompanying drawings, wherein like reference numerals are used for like and corresponding parts, respectively.

Referring to FIG. 1a, there is shown a microchip and differential-type oxygen gas sensor according to the present invention.

As shown in FIG. 1a, the oxygen gas sensor comprises;

a) an alumina substrate 5;

b) a cobalt-plated electrode 13 as a working electrode and Ag/AgCl electrode 12 as a reference electrode, fixed to Ag—Pt layers 11, c) an insulating film 6, deposited over the entire alumina substrate 5, except for the areas of the electrodes 12 and 13 so as to insulate the electrodes.

d) buffered hydrogels 14, placed on the cobalt-plated electrode 13 and Ag/AgCl electrode 12, respectively; and e) hydrogen ion sensitive membranes 15, placed top of each of the electrodes and being more prominent toward the exterior than the insulating film 6.

The cobalt-plated electrode 13 can be preferably fabricated by plating cobalt onto a solid-state electrode material by an electroplating method. More specifically, the cobalt-plated electrode 13 can be fabricated by forming a three-compartment electrode system in which a solid-state metal (Ag—Pt) electrode as a working electrode, an Ag/AgCl electrode as a reference electrode, and a platinum electrode as a auxiliary electrode is dipped into a plating solution saturated with cobalt, and then applying a reduction potential to the three electrodes to reduce cobalt ions to cobalt metal and to form a coating layer onto the surface of metal (Ag—Pt) electrode 11. According to the embodiment of the present invention, it was found that electroplating for 2~4 min gave stable sensitivity to oxygen gas and excellent recovery to its original state.

The buffered hydrogels 14, placed on the cobalt-plated electrode 13 and Ag/AgCl electrode 12, improves the sensitivity of the cobalt-plated electrode 13 to oxygen gas and shortens the hydration time period so that quantification of the content of dissolved oxygen gas can be accomplished in a shorter time. The buffered hydrogel is preferably prepared by dissolving a metal halide, preferably NaCl or KCl, and at least one hygroscopic material into a buffer solution. As a metal halide, but not limited thereto, sodium chloride, potassium chloride or mixture thereof can be mentioned. It can be used in a concentration of 2–5 mM. As a hygroscopic material, but not limited thereto, hydroxyethyl cellulose, polyvinyl alcohol, Methocel (hydroxypropylmethyl cellulose), polyacrylic acid, polyvinylpyrrolidone, polymethylmethacrylate, agar or gelatin can be mentioned.

The ion-sensitive gas-permeable membranes gave ion selectivity to the oxygen gas sensor according to the present invention. As an ion-selective gas-permeable membrane, the one having high adhesiveness that allows the oxygen gas sensor to be fabricated in a flat form is preferable.

The ion-sensitive gas-permeable membrane of the oxygen gas sensor comprises a support polymer, an ion selective material that bonds to a specific ion to cause charge separation in the polymeric membrane, and a plasticizer that serves as a non-volatile organic solvent. Optionally, the ion-selective gas-permeable membrane may further comprise a lipophilic material and an adhesive.

The ion-selective gas-permeable membranes preferred in present invention are hydrogen ion-selective membrane 15 or potassium ion-selective membrane 41. In case of hydrogen ion selective membrane 15, the reference electrode may require the buffered hydrogel layer 14.

According to the preferred embodiment of the present invention, mixture of polyvinyl chloride (PVC) and polyurethane (PU) (tecoflex polyurethane) provide a satisfactory matrix system. The ratio of PVC to PU is preferably 90:10~10:90 by weight. PVC has a superior electrochemical property, but poor in biocompatibility. As thus, when being used in blood or body fluid solely, it may cause proteins to be adsorbed into the electrode membrane, thereby deteriorating the electrochemical properties of the membrane. PU is an adhesive polymer and has excellent biocompatibility. As thus, a combination of PVC and PU increases the adhesion of the ion-selective gas-permeable membrane to the surface of the solid-state electrode and stabilizes the interface between the ion-selective gas permeable membrane and the solid-state electrode to keep electrochemical properties constant, resulting in extending the lifetime of the electrode. The polymer matrixis preferably used in an amount of 32~49% by weight based on the total weight of the ion-selective gas-permeable membrane. For instance, when the content of the polymer matrixis out of this range, the electrochemical stability of the electrode may be lowered.

The ion selective material bonds to a specific ion and causes charge separation in the polymeric membrane such that it enables components in the sample to be tested to be quantitatively determined. A kind of the ion selective material depends on the ions or gas species to be tested and is well known to one of the skilled in the art to which the present invention pertains. For instance, tridodecyl amine (TDDA) as an ion selective material is used for hydrogen ion, valinomycin for potassium ion, 4-tert-butylcalix[4]arene-tetraacetic acid tetraacetyl ester, monensin methyl ester (MME) or N,N,N',N'-tetracyclohexyl-1,2-phenylenedioxydiacetamide (ETH 2120) for sodium ion. Preferably, the ion selective material is used in an amount of 1.0 to 4.5% by weight based on the total weight of the ion-selective gas-permeable membrane. When the ion selective material is used at an amount below or over this range, the membrane may suffer from low ion sensitivity.

As an plasticizer, but not limited thereto, bis(2-ethylhexyl)sebacate (DOS), bis(2-ethylhexyl)adipate (DOA), and 2-nitrophenyl octyl ether (NPOE) can be mentioned. Preferably, the plasticizer can be used in an amount of 50~66% by weight based on the total weight of the ion-selective gas-permeable membrane. An amount out of this range makes the ion selective membrane poor in flexibility.

When the ion selective membrane interacts with a specific ion, undesirable interference from other ions may cause analytical error and may make the sensor useless if such ions are present beyond a tolerable limit. To avoid this problem, a lipophilic material may be added to improve the selectivity of the membrane to a specific ion. Suitable for the present invention is one selected from the group consisting of potassium tetrakis(4-chlorophenyl)borate, sodium tetrakis(3,5-bis(trifluoromethyl)phenylborate, sodium tetraphenylborate, tetradodecylammonium tetrakis(4-chlorophenyl)borate and mixture thereof. Preferably, the lipophilic material is used in an amount of no more than 1.5% by weight based on the total weight of the ion-selective gas-permeable membrane.

Further, a silicon-based adhesive can be also added in order to enhance the adhesiveness of the membrane while maintaining its electrochemical properties. Preferable examples of the adhesive include, but not limited thereto, N-[3-(trimethoxysilyl)propyl]ethylene diamine, and 3-(trimethoxysilyl)propyl methacrylate, and 3-glycidoxypropyltrimethoxysilane. Its amount preferably ranges from 0 to 4.0% by weight based on the total weight of the ion-selective gas-permeable membrane.

The ion-selective gas-permeable membrane can be prepared, for example, by dissolving mixture comprising 32~49% by weight of the support polymer; 1.0~4.5% by weight of the ion selective material; 50~66% by weight of the plasticizer; and 0~1.5% by weight of the lipophilic material into a suitable solvent, and then drying at room temperature.

The present invention also relates to a potentiometric multi-sensor capable of simultaneously detecting two or more ions or gas species including at least the oxygen gas sensor in the present invention.

The potentiometric multi-sensor comprises;

a) an alumina substrate 5;

b) an electrode unit I comprising Ag/AgCl electrode 12 fixed to Ag—Pt layer 11; a hydrogel layer 21, placed on the Ag/AgCl electrode 12; and an aromatic PU membrane 22, deposited over the hydrogel layer 21, which the aromatic PU membrane 22 is enclosed within the well formed by the insulating film 6.

c) an electrode unit II comprising Ag/AgCl electrode 12 fixed to Ag—Pt layer 11; a buffered hydrogel layer 14, placed on the Ag/AgCl electrode 12; and hydrogen ion selective membrane 15, placed top the buffered hydrogel layer 14, which hydrogen ion selective membrane 15 is enclosed within the well formed by the insulating film 6.

d) an electrode unit III comprising Ag/AgCl electrode 12 fixed to Ag—Pt layer 11; a unbuffered hydrogel layer 31, placed on the Ag/AgCl electrode 12; and hydrogen ion selective membrane 15, deposited over the unbuffered hydrogel layer 31, which hydrogen ion selective membrane 15 is enclosed within the well formed by the insulating film 6.

e) an electrode unit IV comprising cobalt-plated electrode layer 13 fixed to Ag—Pt layer 11; a buffered hydrogel layer 14, placed on the cobalt-plated electrode layer 13; and hydrogen ion selective membrane 15, deposited over the buffered hydrogel layer 14, which hydrogen ion selective membrane 15 is enclosed within the well formed by the insulating film 6.

f) an electrode unit V comprises Ag/AgCl electrode 12 fixed to Ag—Pt layer 11; potassium ion selective membrane 41 deposited over the Ag/AgCl electrode 12, which potassium ion selective membrane 41 is enclosed within the well formed by the insulating film 6.

g) an insulating film 6, deposited over the entire alumina substrate 5, except for the areas of the electrode units so as to insulate the electrode units I~V.

Figure 1B:
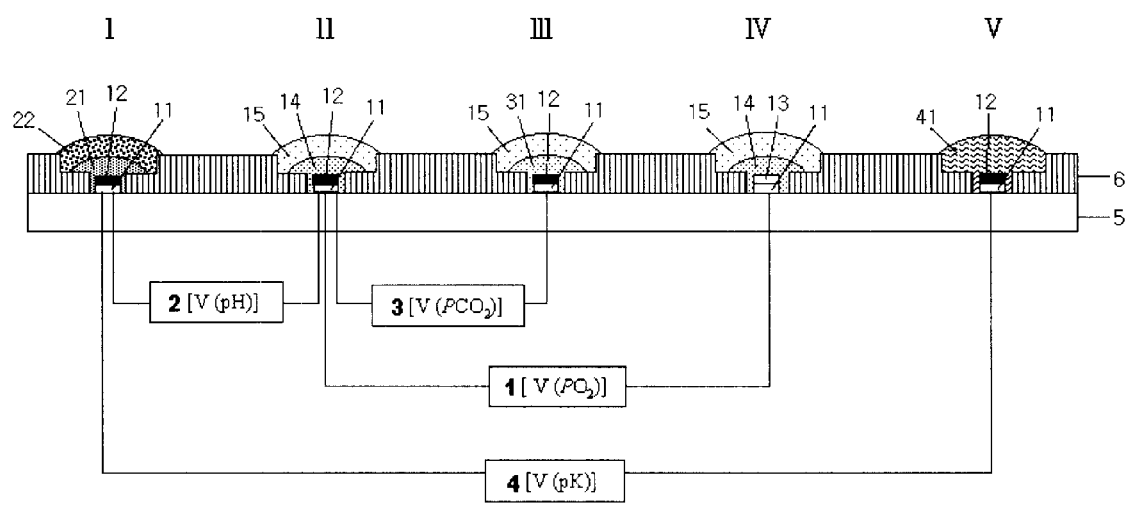

The potentiometric multi-sensor according to present invention functions as the sensor for hydrogen ion, potassium ion, oxygen gas and carbon dioxide. This is shown in FIG. 1b.

Wherein the oxygen gas sensor 1 within the potentiometric multi-sensor composes of an electrode unit IV as a working electrode and an electrode unit II as a reference electrode. Its oxygen gas sensor can measure the content of oxygen gas dissolved in a sample solution by potential difference between the cobalt-plated working electrode 13 and the Ag/AgCl reference electrode 12.

The pH sensor 2 in the potentiometric multi-sensor comprises an electrode unit II as a working electrode and an electrode unit I as a reference electrode.

In electrode unit I, the hydrogel layer 21 is selected from the group consisting of EPPS N(2-hydroxyethyl)piperazine-N'-(3-propanesulfonic acid)-NaOH, MES 2-(N-morpholino) ethanesulfonic acid-NaOH, and KHP potassium hydrogen phthalate-NaOH.

The carbon dioxide sensor 3 in the potentiometric multi-sensor makes a combination of an electrode unit III as a working electrode and an electrode unit II as a reference electrode.

The electrode unit II comprises Ag/AgCl electrode 12 fixed to Ag—Pt layer 11; a buffered hydrogel layer 14, placed on the Ag/AgCl electrode 12; and hydrogen ion selective membrane 15, placed top the buffered hydrogel layer 14.

Wherein the electrode unit III includes an unbuffered hydrogel layer 31 comprising $2.4 \times 10^{-2}$~$8.1 \times 10^{-2}\%$ by weight (3~10 mM) of sodium bicarbonate, $5.6 \times 10^{-4}$~$5.6 \times 10^{-3}\%$ by weight (0.1~1.0 mM) of sodium chloride or potassium chloride and 1~4% by weight of a hygroscopic material, and carbonic anhydrase in an amount of 0.1~6.0 mg per ml of the hydrogel. As the hygroscopic material, but not limited thereto, hydroxyethyl cellulose, poly (vinyl alcohol), Methocel ((hydroxypropyl) methyl cellulose), polyacrylic acid, polyvinylpyrrolidone, poly (methylmethacrylate), agar and gelatin can be mentioned.

The electrode unit II can function simultaneously as a reference electrode or a working electrode according to detecting for hydrogen ion, oxygen gas, and carbon dioxide. In this connection when an ion/gas non-sensitive reference electrode is introduced, such as the oxygen non-sensitive ion selective electrode, which serves as the reference electrode in the oxygen gas sensor 1, can be used as another working electrode in pH sensor 2, and as a reference electrode in carbon dioxide gas sensor 3. Based on the results, the electrode unit II can realize a microchip-based differential-type potentiometric multi-sensor.

In addition, the pK sensor 4 in the multi-sensor comprises an electrode unit V as a working electrode and an electrode unit I as a reference electrode.

In this manner, a microchip-based potentiometric multi-sensor capable of detecting two or more ions and gas species, simultaneously, can be achieved on a single chip and find numerous applications in blood analysis and clinical sample analysis.

A better understanding of the present invention may be obtained in light of the following examples which are set forth to illustrate, but are not to be construed to limit the present invention.

EXAMPLE 1

Oxygen Sensitivity of Cobalt Electrode with Respect to Electroplating Time

To be used as a working electrode, a cobalt electrode was prepared by an electroplating method. The effect of the electroplating time period on the sensitivity of oxygen for the cobalt electrode was examined through the following experiment.

A homogeneous mixture of 10 mg of platinum and 90 mg of silver was screen-printed on an alumina substrate to form electrode layers, followed by introducing an insulating film onto the aluminum substrate through a screen-printing method to separate the electrode layers from each other. Across a three-compartment electrode system in which the solid-state metal (platinum-silver) electrode was used as a working electrode, an Ag/AgCl electrode as a reference electrode, and a platinum electrode (1 cm$^2$) as an auxiliary electrode, the potential was applied on −1.5 V for 1~5 min, so as to plate cobalt onto the solid-state Pt—Ag electrode. For the electroplating, a saturated cobalt salt solution containing 1.8 M $CoSO_4 \cdot 7H_2O$, 0.3 M NaCl and 16 mM $H_3BO_3$ was used as a plating solution.

Figure 2:
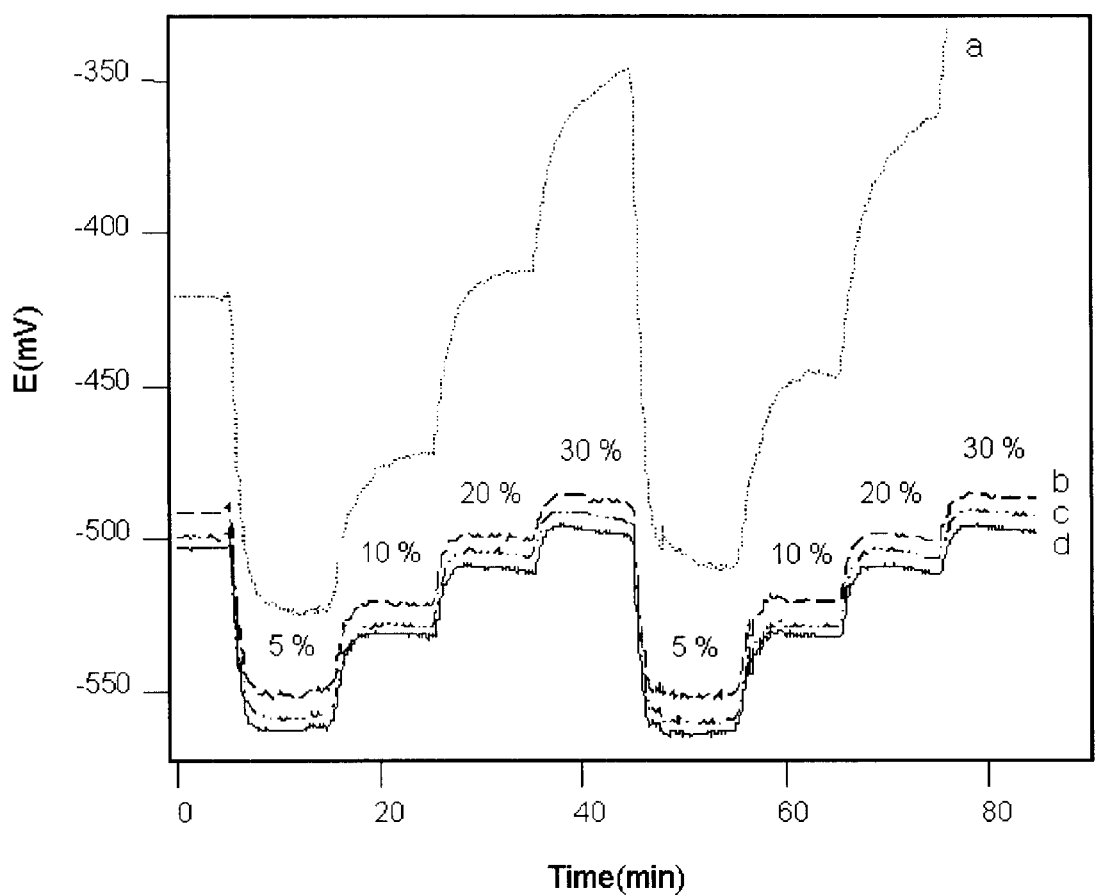
FIG. 2 is a graph showing the sensitivity of the oxygen gas sensor according to the present invention, which cobalt is plated for 1 min (a), 2 min (b), 3 min (c), and 4 min (d).

When the plating time was extended to 5 min or longer, cobalt was plated even onto the alumina substrate beyond the platinum-silver electrode. Thus, the plating was preferably stopped within less than 5 min. A measurement was made for the sensitivity of oxygen of the cobalt electrode according to the plating time period. As shown in FIG. 2, the cobalt electrodes that plated for 2~4 min showed stable sensitivity for oxygen gas and excellent recovery, but the cobalt electrode that plated for as short as 1 min was unstable in the sensitivity of oxygen and recovery. For the evaluation of the oxygen sensitivity, the levels of dissolved oxygen in sample solutions were set at 5%, 10%, 20% and 30% by controlling the amounts of oxygen gas and nitrogen gas, and the measurement was conducted in a stationary system.

EXAMPLE 2

Oxygen Sensitivity Dependence of the Composition of Buffered Hydrogel

An oxygen gas sensor is fabricated by including the cobalt-plated electrode prepared in Example 1, a buffered hydrogel and an ion selective membrane. The sensitivity of oxygen according to the buffer composite of the buffered hydrogel was examined as follows.

Polyvinylpyrrolidone was dissolved at an amount of 6% by weight in a buffer solution containing 5 mM potassium chloride to give a buffered hydrogel, which was then loaded on the cobalt-plated electrode and dried for 4 min to prepare an electrolyte layer for microchip-based flat electrodes. As the buffer solution, 0.2 M EPPS (N-(2-hydroxyethyl) piperazine-N'-(3-propanesulfonic acid))-NaOH pH 7.9; 0.2 M MES (2-(morpholino)ethanesulfonic acid)-NaOH, pH 5.5; or 0.2 M KHP (potassium hydrogen phthalate)-NaOH, pH 4.0.

To provide hydrogen ion selective membrane 15 in an oxygen gas sensor, the hydrogen ion selective membrane 15 was dissolved to a 800 μl of tetrahydrofuran solution comprising a combination of 10.7 mg of PVC and 49.5 mg of PU as the polymer matrix, 6 mg of TDDA (tridodecyl amine) as an ion selective material, 75.0 mg of NPOE (2-nitrophenyl octyl ether) as a plasticizer, 1.4 mg of KTpClPB (potassium tetrakis [4-chlorophenyl] borate) as a lipophilic additive, and 2.0 g of Z-6020 (N-(trimethoxysilyl)propyl)ethylene diamine) as an adhesive, and followed by drying the solution at room temperature for 1 day. Hydrogen ion selective membrane 15 as above prepared was placed top buffered hydrogel layers 14.

Figure 3A:
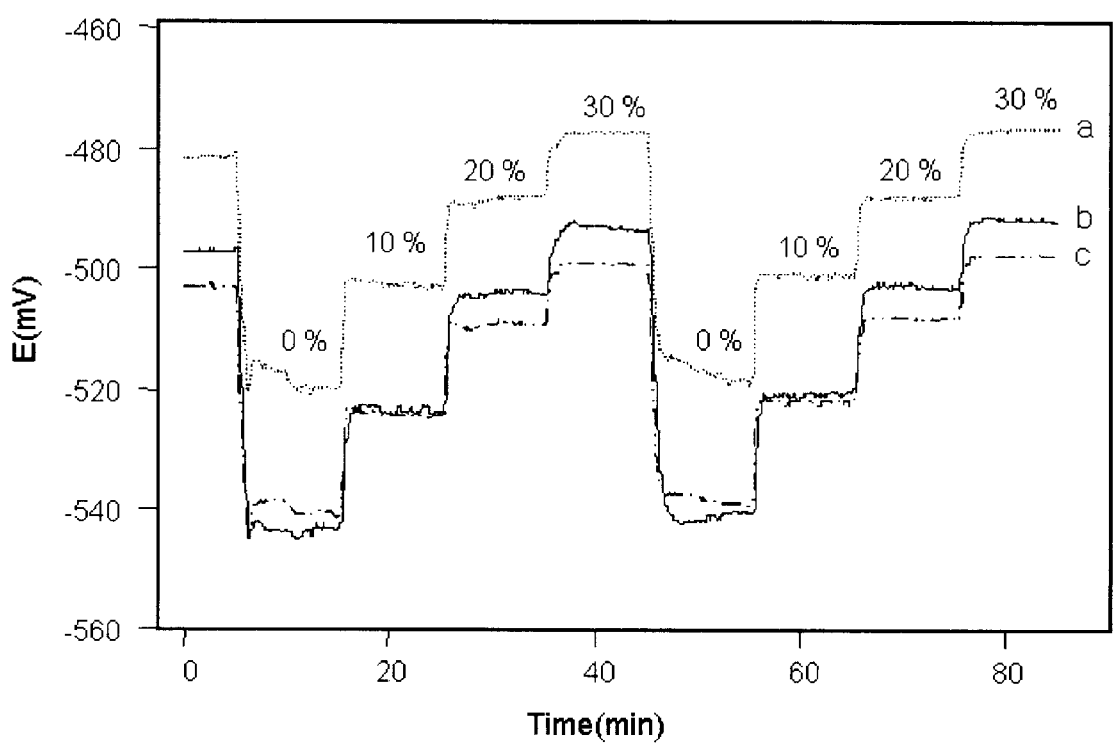
FIG. 3$a$ is a graph showing the sensitivity of the oxygen gas sensor which employs a buffered hydrogel comprising, as a buffer solution, (a) 0.2 M EPPS N(2-hydroxyethyl) piperazine-N'-(3-propanesulfonic acid)-NaOH, pH 7.9; (b) 0.2 M MES 2-(N-morpholino)ethanesulfonic acid-NaOH, pH 5.5; and (c) 0.2 M KHP potassium hydrogen phthalate-NaOH, pH 4.0.
Figure 3B:
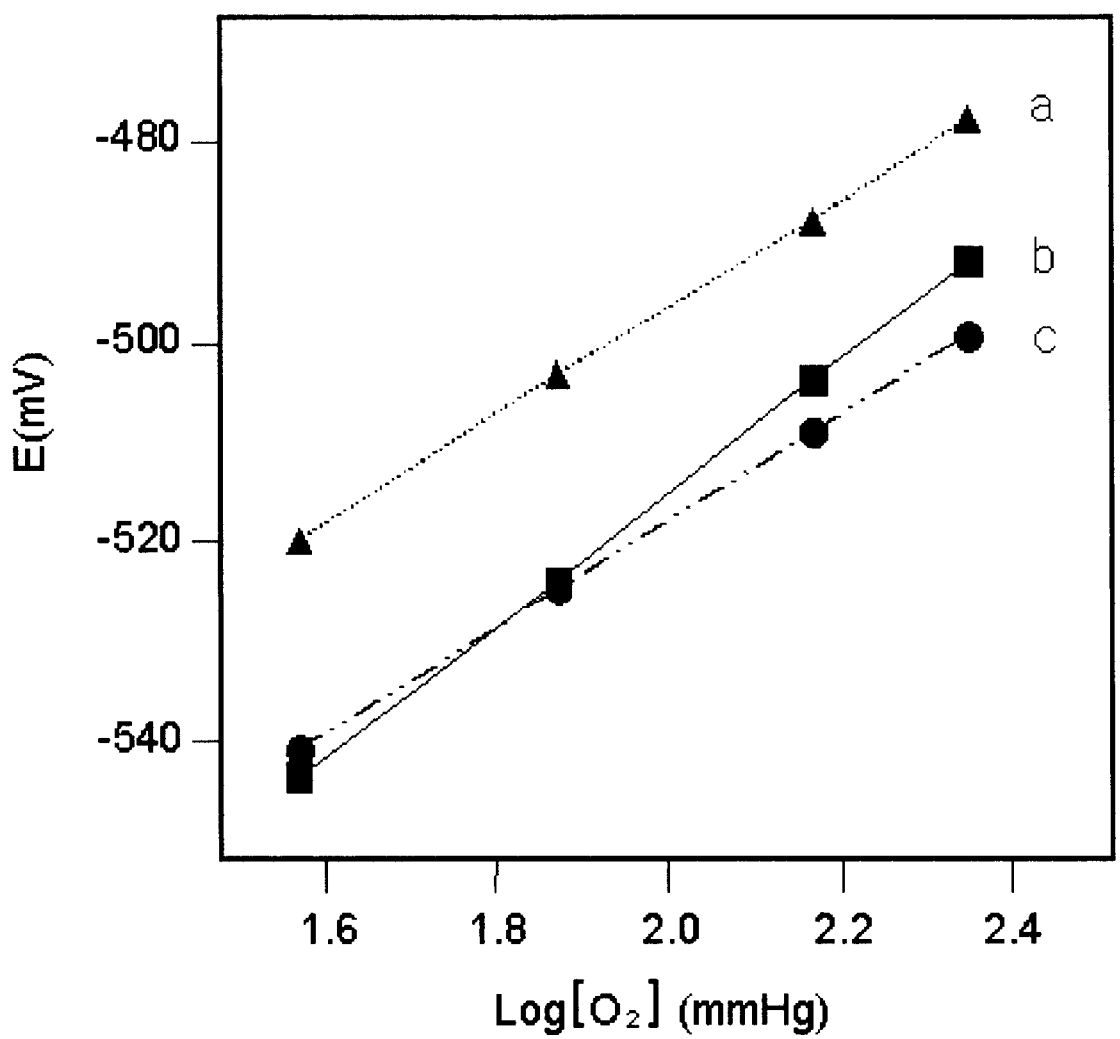

The working electrode was tested for the effect in the sensitivity of oxygen according to the content of oxygen dissolved in a sample solution, as in Example 1. The results are given in FIGS. 3a and 3b. As shown in the graphs, all of the working electrodes employing as a buffer solution for the buffered hydrogel 0.2 M EPPS-NaOH, pH 7.9 (a), 0.2 M MES-NaOH, pH 5.5 (b) and 0.2 M KHP-NaOH, pH 4.0 (c) were found to be superior in sensitivity and recovery rate, exhibiting the slope of sensitivity of 55 mV/dec. or greater with the best results obtained from 0.2 M MES-NaOH pH 5.5.

EXAMPLE 3

Selectivity for Specific Ions of Working and Reference Electrodes Containing Ion-selective Gas-permeable Membrane With the introduction of Hydrogen ion selective membrane 15 or potassium ion selective membrane 41 in an oxygen gas sensor, its selectivity for each ion species was examined as follows.
(1) Selectivity for Hydrogen Ion of Working and Reference Electrodes Containing Hydrogen Ion-Selective Membrane The buffered hydrogel 14 showing the most excellent sensitivity in Example 2 and a hydrogen ion-selective membrane 15 were introduced to a cobalt-plated electrode 13 to give a working electrode for oxygen gas sensors. Subsequently, the solid-state electrode was immersed in a 1 M $FeCl_3$ solution for 2 min to form a layer of AgCl, insoluble metal salt layer, thereon, followed by loading the buffered hydrogel 14 and hydrogen ion-selective membrane 15 as same in the working electrode to produce a reference electrode.

Since the a reference electrode for oxygen sensor has hydrogen ion-selective membrane 15 and carbon dioxide gas penetrated through the hydrogen ion-selective membrane 15 changes the hydrogen ion concentration at the membrane/electrode interface, the oxygen sensor system may exhibit poor sensitivity. Therefore, it was preferred that the same acidic-buffered hydrogel 14 as in the working electrode is placed between the reference electrode and the hydrogen ion-selective membrane 15.

Figure 4A:
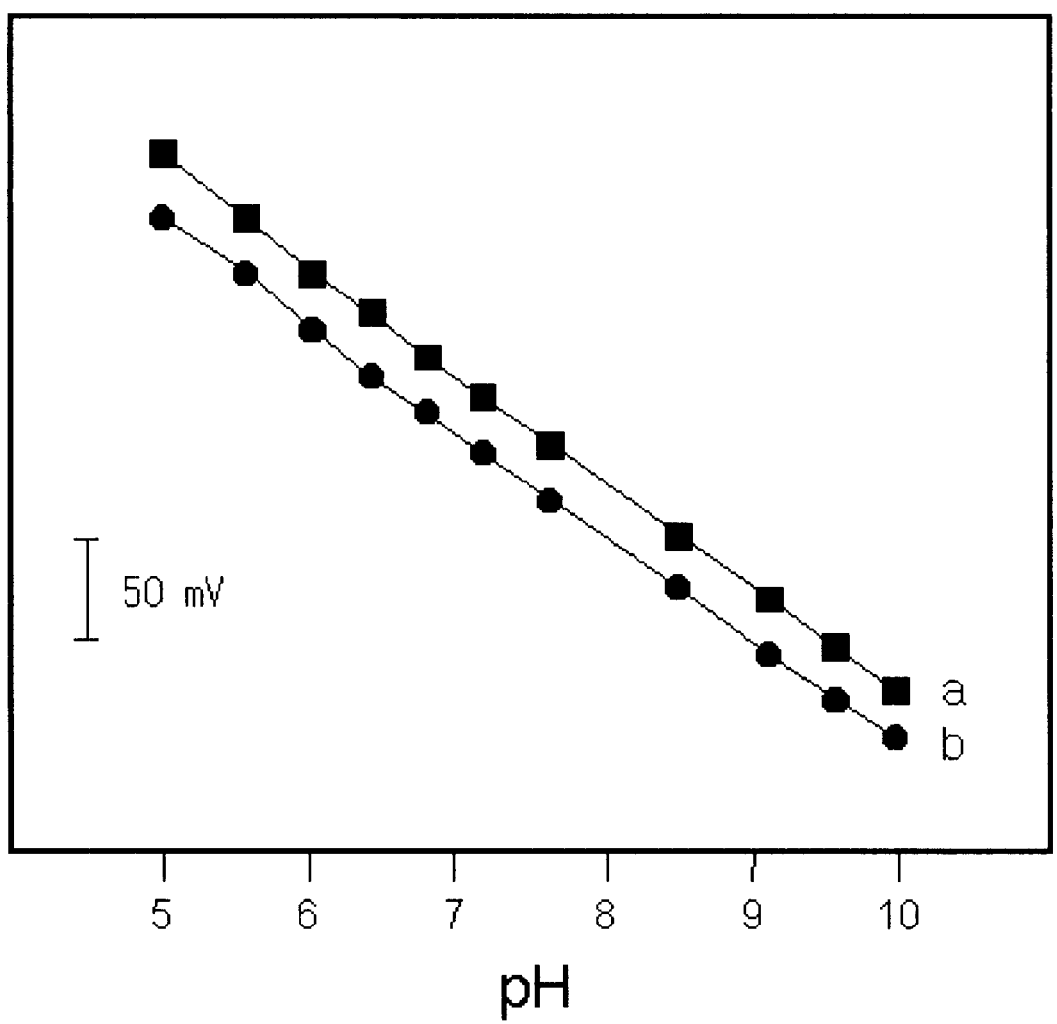
FIG. 4$a$ is a graph showing the sensitivity for hydrogen ion of a reference electrode (a) and a working electrode (b), each containing a hydrogen ion selective membrane 15.

Using the reference electrode and the working electrode prepared as above as examined over the pH range of 5~10, and the results are given in FIG. 4a. As apparent from the linear curves of FIG. 4a, the reference electrode (a) and the working electrode (b) were both superior in the selectivity for hydrogen ions. In addition, their same patterns of sensitivity offer the possibility of the introduction of a differential-type oxygen gas sensor.
(2) Potassium Selectivity of Working and Reference Electrodes Containing Potassium Ion-selective Membrane The buffered hydrogel 14 showing the most excellent sensitivity in Example 2 was introduced to a cobalt-plated electrode. Subsequently, potassium ion selective membrane 41 was prepared in a 800 μl of tetrahydrofuran solution comprising a combination of 10.7 mg of PVC and 49.5 mg of PU as the polymer matrix, 1 mg of valinomycin (potassium ionophore I) as a potassium ion selective material, 132.0 mg of DOA (bis(2-ethylhexyl)adipate) as a plasticizer. The potassium ion selective membrane 41 prepared as above was introduced to a cobalt-plated electrode 13 to give a working electrode for oxygen gas sensors.

Separately, the solid-state electrode was immersed in a 1 M $FeCl_3$ solution for 2 min to form a layer of AgCl, insoluble metal salt, thereon, followed by providing the same potassium ion selective membrane 41 for the AgCl layer to produce a reference electrode, without hydrogel layer.

Figure 4B:
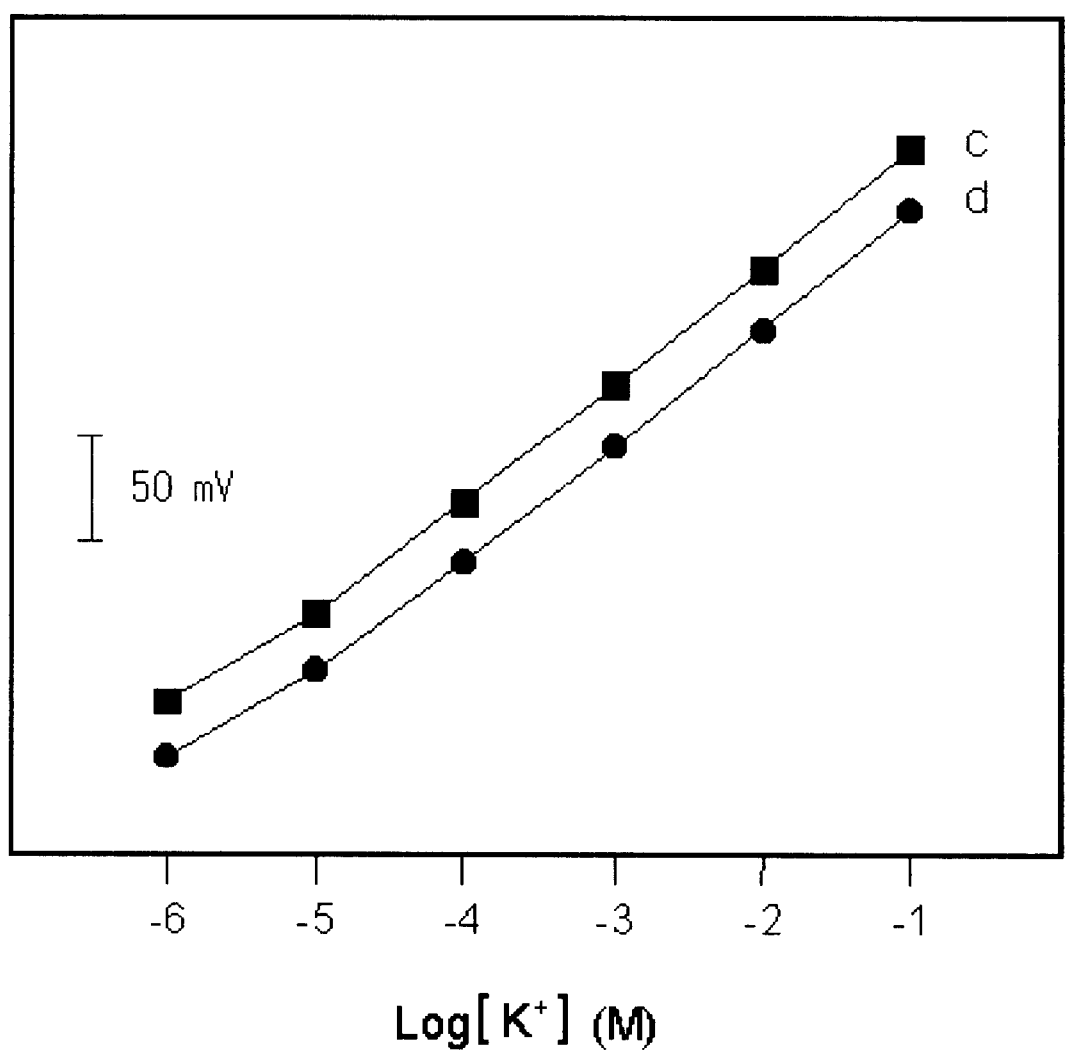

Using the reference electrode and the working electrode, the sensitivity for potassium ions was examined over the level of potassium ion ranged from $1\times10^{-6}$ M to $1\times10^{-1}$ M, and the results are given in FIG. 4b. As apparent from the linear curves of FIG. 4b, the reference electrode (c) and the working electrode (d) were both superior to the selectivity for potassium ion. In addition, their same patterns for sensitivity offer the possibility of the introduction of a differential-type oxygen gas sensor.

EXAMPLE 4

Electroanalytical Characteristics of Microchip-based Differential-type Oxygen Gas Sensor in Flow Injection Analysis System The microchip-based differential-type oxygen gas sensor of the present invention was characterized for its electroanalytical performance as follows.

Figure 5A:
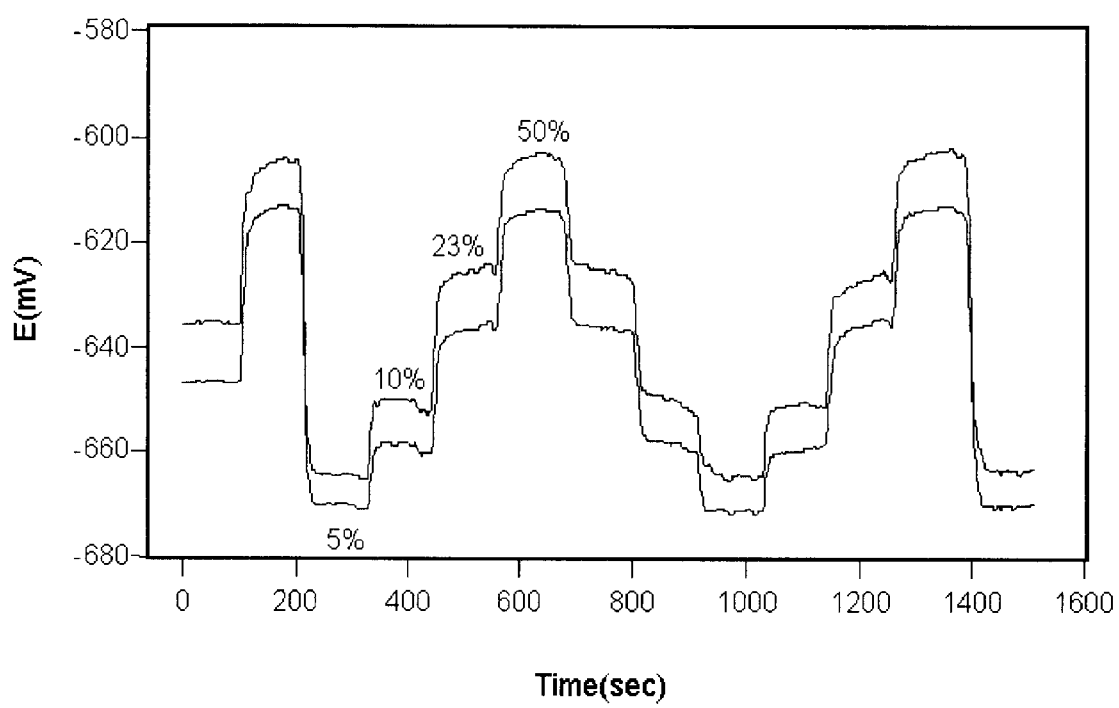
Figure 5B:
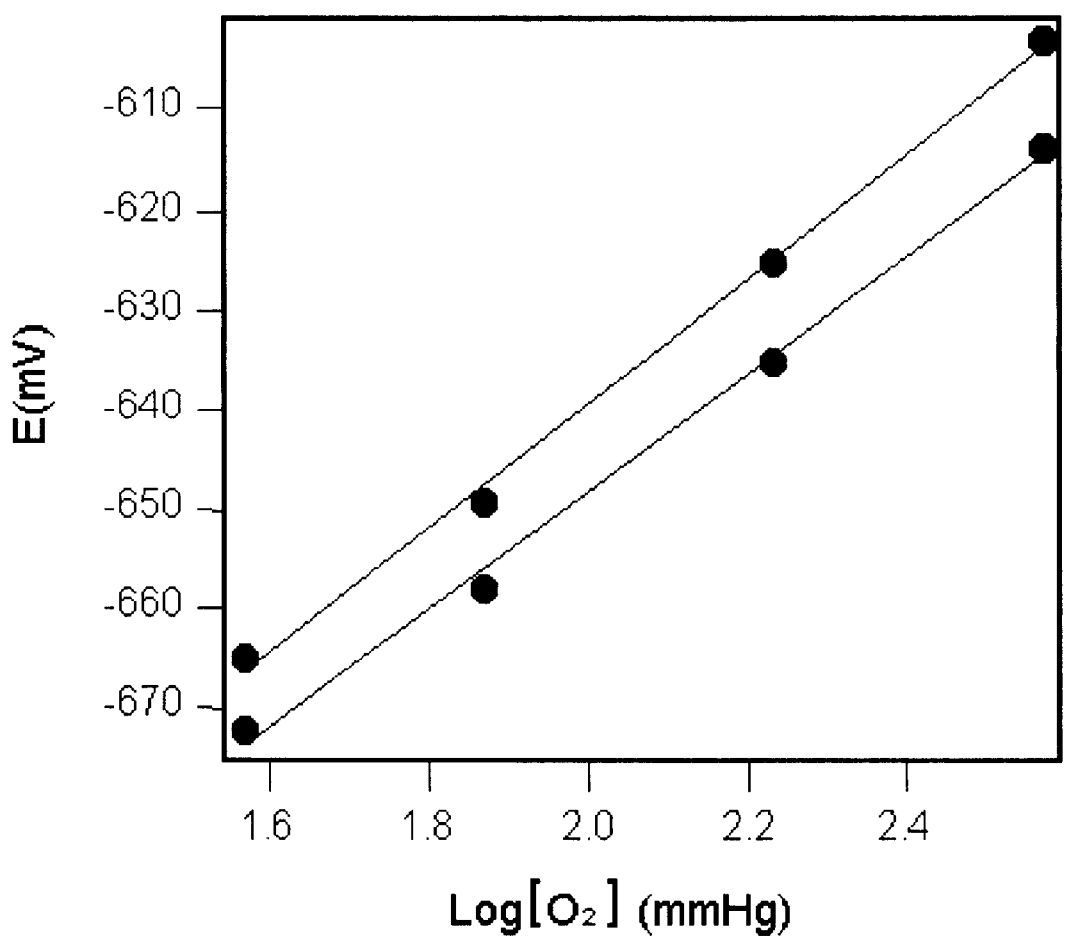

A microchip-based differential-type oxygen gas sensor composed of the reference electrode and working electrode prepared in Example 3 (1) was measured for sensitivity and recovery through the flow injection analysis in which sample solutions with level of oxygen of 5%, 10%, 23%, and 50% were injected to the sensing portion of the oxygen gas sensor. The measurement results are given in FIGS. 5a and 5b. As apparent from the graphs of FIGS. 5a and 5b, the oxygen gas sensor exhibited quick response to the change of oxygen concentration and quickly returned to original states with the slope of sensitivity ranging from 59.0 to 64.2 mV/dec.

EXAMPLE 5

Lifetime of Microchip-based Differential-type Oxygen Gas Sensor

The microchip-based differential-type oxygen gas sensor of the present invention was measured for lifetime in the following manner.

Figure 6:
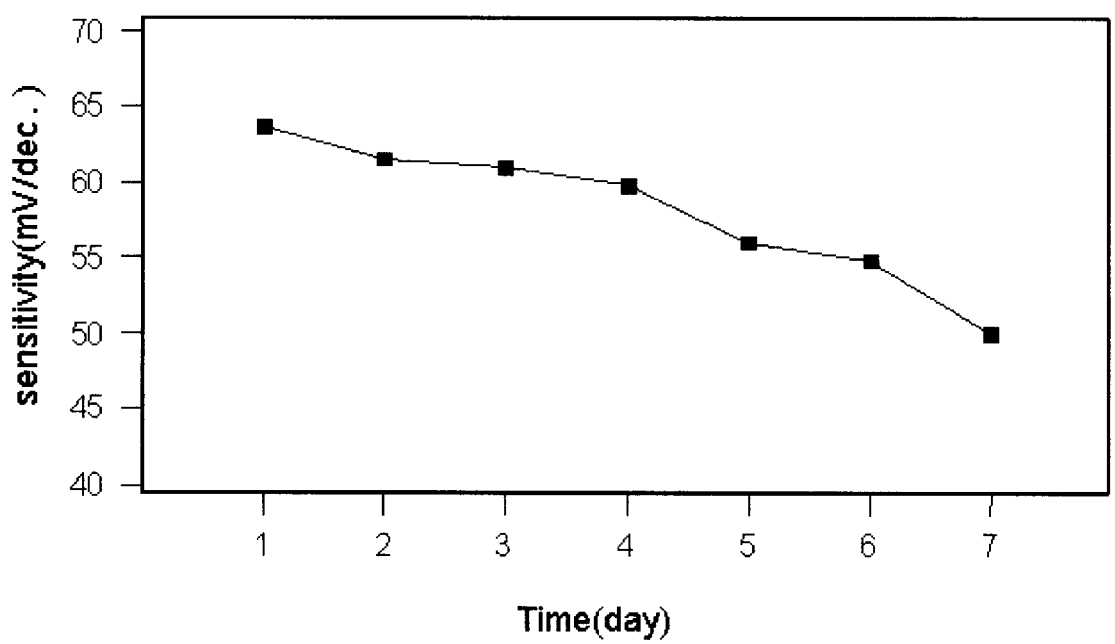
FIG. 6 is a curve showing the lifetime of the oxygen gas sensor, according to selectivity for oxygen gas versus time (days).

To determine the lifetime of the microchip-based differential-type oxygen gas sensor described in Example 4, its change in sensitivity of oxygen was examined with time (days). The results are shown in FIG. 6. As shown in the curve of FIG. 6, the microchip-based differential-type oxygen gas sensor maintained its sensitivity of oxygen at 50 mV/dec and higher for 7 days.

EXAMPLE 6

Measurement of Oxygen Level in Unknown Sample Solution

The microchip-based differential-type oxygen gas sensor of the present invention was used to measure the oxygen level of an unknown sample solution and its accuracy was assayed as follows.

Figure 7A:
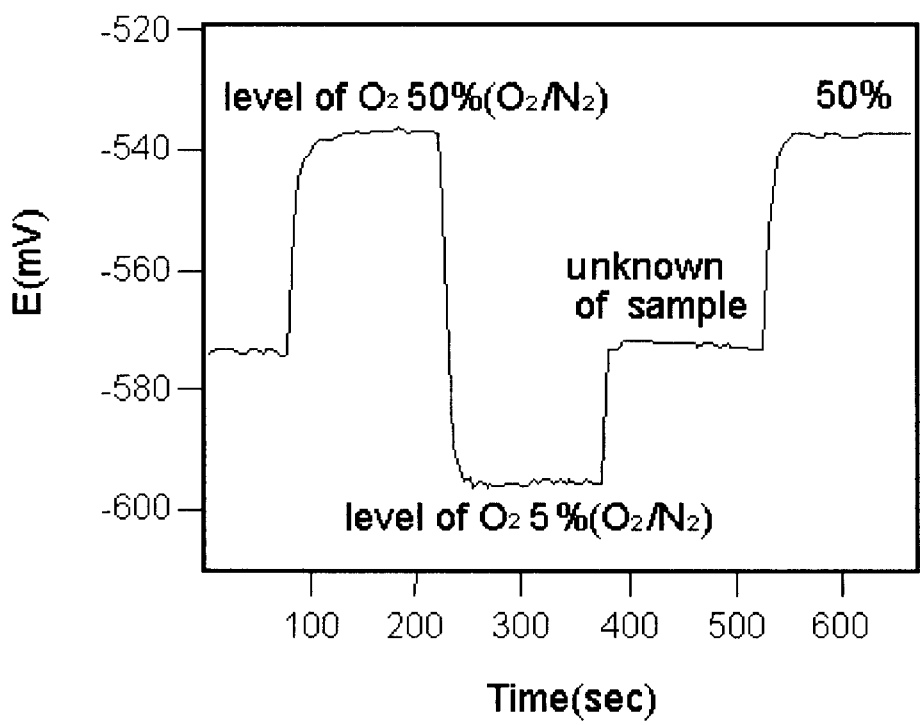
FIG. 7a is a curve showing the sensitivity of oxygen gas sensor for measuring the levels of oxygen in unknown sample.
Figure 7B:
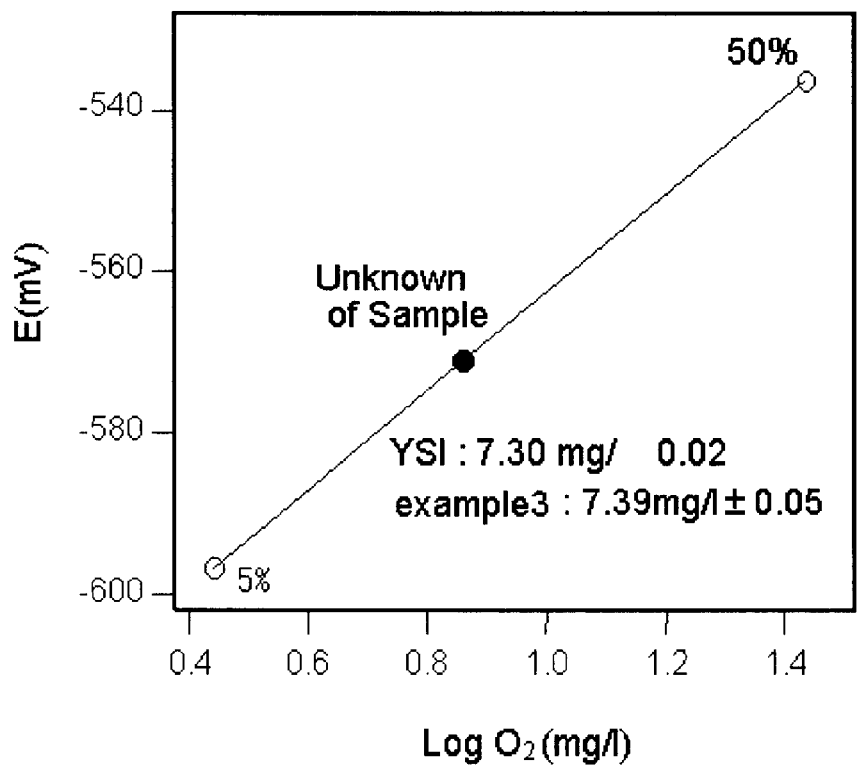
FIG. 7b is a calibration curve for the oxygen sensitivity shown in FIG. 7a, in which the sensitivity of the oxygen gas sensor is compared with that of a commercially available oxygen meter (YSI DO meter Model 52).

With solutions containing the content of oxygen 5% and 50%, the potential of each solution was measured through a flow injection analysis, as shown in FIG. 7a. From the potential, a calibration curve was obtained as shown in FIG. 7b. Based on this calibration curve, an unknown sample solution was determined to have an oxygen concentration of 7.39±0.05 mg/l averaged from five oxygen gas sensors. Meanwhile, the level of oxygen for unknown sample solution was found to be 7.30±0.05 mg/l as measured by a commercially available oxygen meter (YSI DO meter Model 52), which is extensively used in hospitals. Similarity between the two measured oxygen levels may be taken as a proof that the microchip-based differential-type oxygen gas sensor of the present invention is reliable.

7

Fabrication of Microchip-based Potentiometric Sensor and Measurement for Sensitivity Based on the microchip-based differential-type oxygen gas sensor, the present invention provides a microchip-based potentiometric multi-sensor capable of detecting two or more ions and gas species simultaneously such as hydrogen ion, carbon dioxide gas, oxygen gas, and potassium ion.

(1) Preparation of Ion/Gas Non-sensitive Reference Electrode

As one of the solid-state electrodes, an AgCl metal layer, insoluble salt layer, was formed on a single chip and subsequently was introduced to a hydrogel layer 21 prepared by dissolving 6% by weight of polyvinylpyrrolidone in 2 M potassium chloride. On the hydrogel layer 21, ion/gas non-sensitive aromatic PU (polyurethane) membrane 22 was provided as an outer membrane. The resulting electrode was used as a reference electrode for hydrogen ion sensor 2 and for potassium ion sensor 4 in a microchip-based potentiometric sensor.

(2) Preparation of pH Sensor

One of the solid-state electrodes formed on a single chip was converted into an AgCl metal layer, insoluble salt layer to produce a working electrode for pH sensor 2. The buffered hydrogel layer 14 and hydrogen ion selective membrane 15 as the same composition in the reference electrode of the oxygen gas sensor prepared in Example 3 (1) was introduced. In addition to being a working electrode against the ion/gas non-sensitive reference electrode, the pH sensor 2 prepared as above would serve as a reference for a differential-type oxygen gas sensor.

(3) Preparation of Differential-type Carbon Dioxide Gas Sensor

In a differential-type carbon dioxide gas sensor 3, the quantitative analysis of carbon dioxide is, in principle, conducted by measuring the levels of hydrogen ion that generated by which carbon dioxide penetrates a hydrogen ion-selective membrane 15 and thus hydrates at an unbuffered hydrogel layer 31 inside the membrane.

One of the solid-state electrodes formed on a single chip was converted into an AgCl metal layer, insoluble salt layer. Separately, 6% by weight of polyvinylpyrrolidone was dissolved in a solution containing $4.0\times10^{-2}$% by weight (5.0 mM) of sodium bicarbonate and $2.8\times10^{-3}$% by weight (0.5 mM) of sodium chloride (or potassium chloride) to give a hydrogel. The unbuffered hydrogel layer 31 was prepared that 0.1 mg (0.28 mg/ml) of carbonic anhydrase was added to 350 μl of the hydrogel. The resulting unbuffered hydrogel layer 31 was loaded onto the Ag/AgCl electrode layer 12, and followed by providing hydrogen ion-selective membrane 15 to yield a working electrode for a differential-type carbon dioxide gas sensor. Like the oxygen gas sensor, the differential-type carbon dioxide gas sensor 3 was performed a differential manner while employing the working electrode of the pH sensor as a reference electrode.

(4) Preparation of Differential-type Oxygen Gas Sensor

To the cobalt electrode plated in the same manner as in Example 1, the buffered hydrogel layer 14 and hydrogen ion-selective membrane 15 showing the most excellent sensitivity in Example 2 were introduced to prepare a working electrode for a differential-type oxygen gas sensor.

(5) Preparation of Potassium Ion Sensor

One of the solid-state electrodes formed on a single chip was converted into an AgCl metal layer, insoluble salt layer and followed by introducing potassium ion selective membrane 41 as the same composition in Example 3 (2) to prepare a working electrode for a potassium ion sensor.

(6) Measurement of Sensitivity of Microchip-based Potentiometric Sensor

Using sample solutions 1, 2 and 3, which were different in ion/gas levels from one another, an examination was conducted of the sensitivity for hydrogen ion, carbon dioxide gas, oxygen gas and potassium ion of the microchip-based potentiometric multi-sensor prepared in (1)~(5). The results are shown in FIGS. 8a and 8b.

Figure 8A:
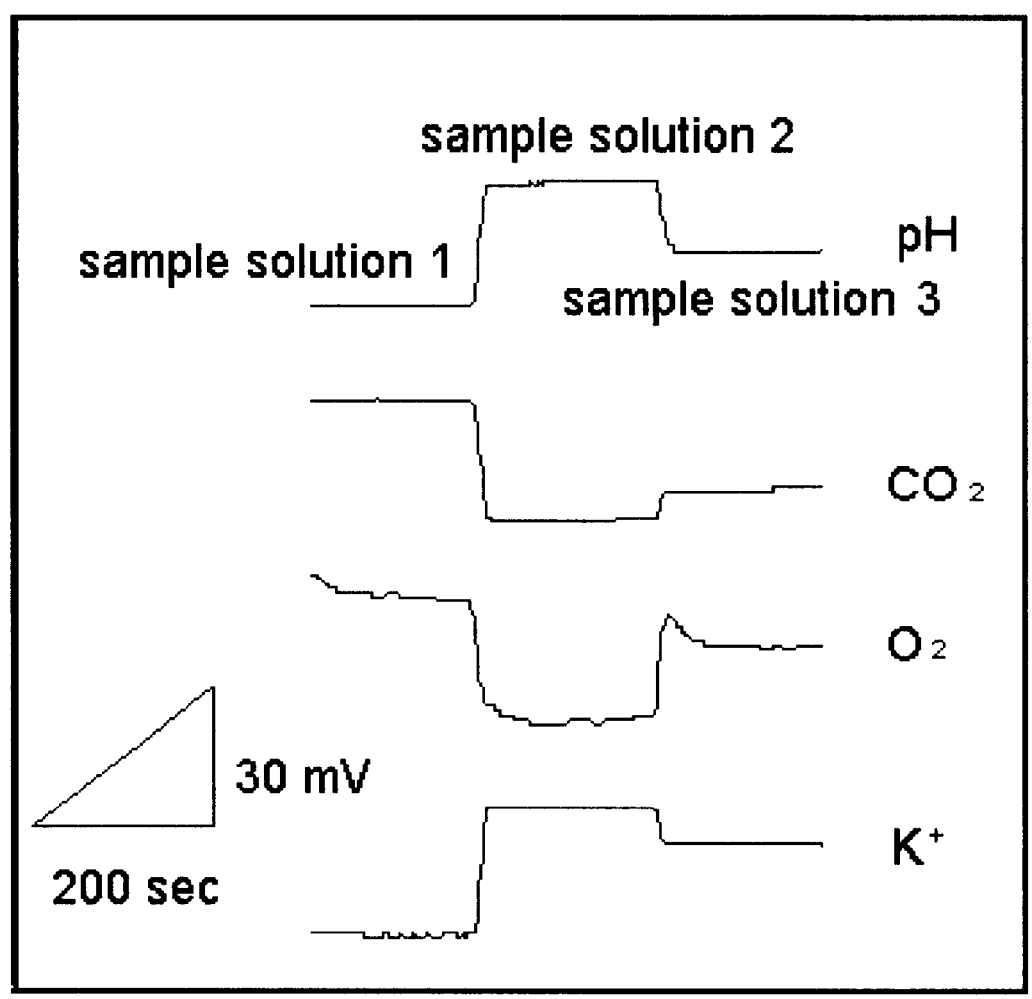
FIG. 8a is a graph showing the sensitivity of a microchip-based potentiometric multi-sensor for measuring two or more ions and gas species, such as hydrogen ion, carbon dioxide gas, oxygen gas and potassium ion.
Figure 8B:
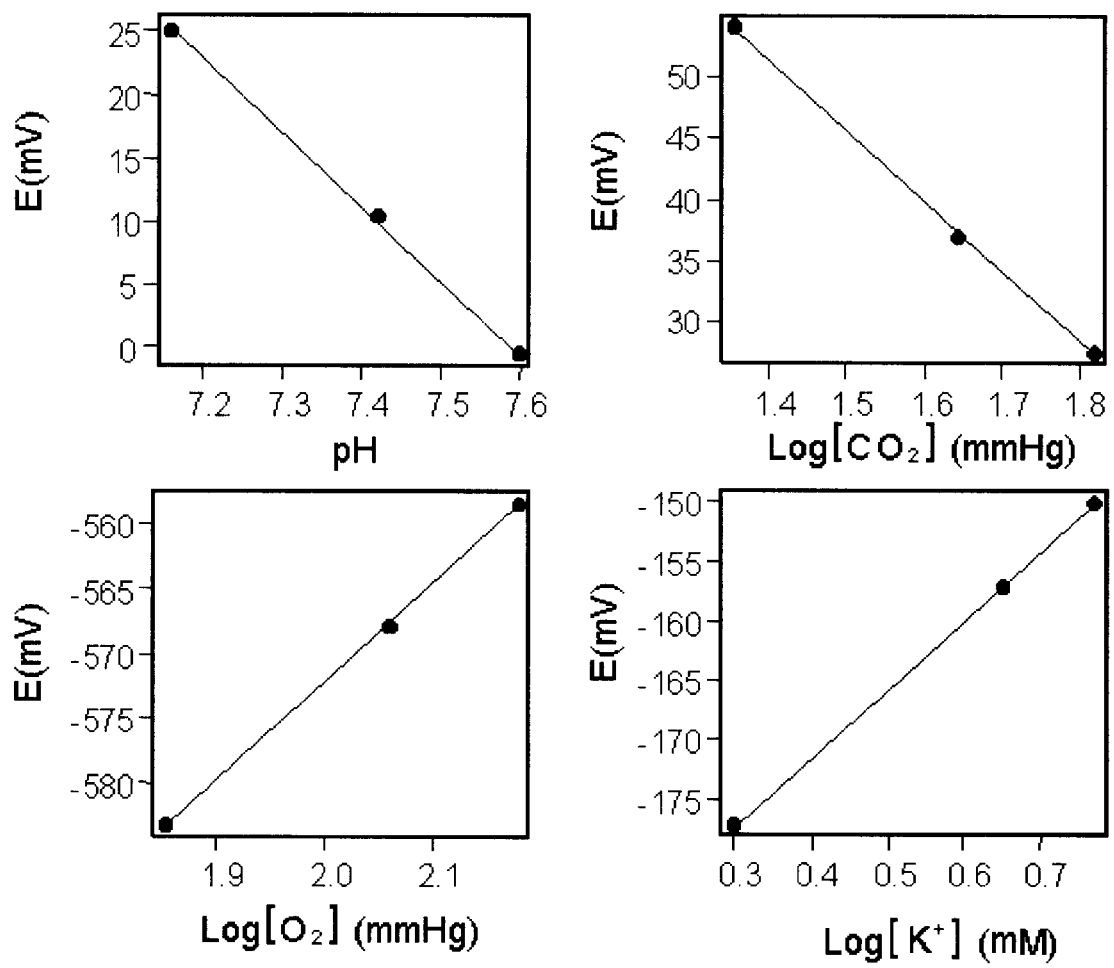

FIG. 8a shows the microchip-based potentiometric multi-sensor's sensitivity for hydrogen ion, carbon dioxide gas, oxygen gas and potassium ion according to a flow injection analysis.

From the sample solutions 1, 2, and 3 containing different concentration of ion/gas species, the microchip-based potentiometric multi-sensor quickly and stably responds to changes in levels of hydrogen ion, carbon dioxide gas, oxygen gas, and potassium ion. In FIG. 8b, there are calibration curves for FIG. 8a, each of which has such linearity that the microchip-based potentiometric multi-sensor turned out to be superior to sensitivity for hydrogen ion, carbon dioxide gas, oxygen gas and potassium ion, which were contained at different concentrations in sample solutions 1, 2, and 3 (see Table 1). In addition, in spite of small amounts (3 ml) of samples, the microchip-based potentiometric multi-sensor accurately and quickly detected the levels of species of interest, and thus can be useful as a sensor for multi-blood analysis and clinical analysis.

TABLE 1

Composition of Assay Solution

| Composition | Content | | |
| --- | --- | --- | --- |
| | Sample solution 1 | Sample solution 2 | Sample solution 3 |
| pH($-\log[H^+]$) | 7.61 | 7.15 | 7.42 |
| $pco_2$(mmHg) | 22 | 66 | 42 |
| $pO_2$(mmHg) | 153 | 73 | 116 |
| $Na^+$ (mM) | 155.9 | 126.9 | 140.5 |
| $K^+$ (mM) | 2.05 | 5.88 | 4.50 |
| $Ca^{2+}$ (mM) | 0.53 | 1.52 | 1.12 |

As described hereinbefore, the oxygen gas sensor of the present invention comprises a working electrode composed of a cobalt-plated electrode, a buffered hydrogel, and an ion-selective gas-permeable membrane and a reference electrode composed of an oxygen non-sensitive silver chloride electrode and the ion-selective gas-permeable membrane. Over conventional ones, the oxygen gas sensor of the present invention has the advantage of being applied to a microchip-based sensor. In the solid-state structure, the sensing part responsible for detecting a species of interest is so small that quantitative analysis for oxygen can be achieved with a very small quantity (2~4 ml) of a sample. Thus, the sensor can find applications in multi-blood analysis and clinical sample analysis. Moreover, the solid-state sensor structure enables the development of microchip-based potentiometric sensors that are able to detect multi ions and gas species on a single chip, as well as being advantageous in mass production, thereby significantly reducing the production cost.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A microchip-based differential oxygen gas sensor comprising a working electrode and a reference electrode, wherein
   a) the working electrode comprises a cobalt-plated electrode 13 on a Ag—Pt layer, a buffered hydrogel layer 14, and an ion-selective gas-permeable membrane; and
   b) the reference electrode comprises a Ag/AgCl electrode 12 on a Ag—Pt layer, which is non-selective to oxygen gas, a buffered hydrogel layer, which is made of the same material as the buffered hydrogel layer of the working electrode, and an ion-selective gas-permeable membrane, which is made of the same material as the ion-selective gas-permeable membrane of the working electrode, wherein the buffered hydrogel layer comprises a buffer solution containing 2–5 mM of sodium chloride or potassium chloride, and 2–7% by weight of a hygroscopic material.

2. The microchip-based differential oxygen gas sensor as set forth in claim 1, wherein the ion-selective gas-permeable membrane is selected from hydrogen ion selective membrane 15 or potassium ion selective membrane 41.

3. The microchip-based differential oxygen gas sensor as set forth in claim 1, comprising:
   a) an alumina substrate 5 on which the electrodes are arranged, and
   b) an insulating film 6, deposited over the entire alumina substrate 5, except for the areas of the electrodes 12 and 13 so as to insulate the electrodes,
   whereby the ion-selective membranes are hydrogen ion sensitive membranes 15, placed top of each of the electrodes and are enclosed in a well formed by the insulating film 6.

4. The microchip-based differential oxygen gas sensor as set forth in claim 1, wherein the hygroscopic material is selected from the group consisting of hydroxyethyl cellulose, poly (vinyl alcohol), ((hydroxypropyl) methyl cellulose), polyacrylic acid, polyvinylpyrrolidone, poly (methylmethacrylate), agar and gelatin.

5. The microchip-based differential oxygen gas sensor as set forth in claim 1, wherein the ion-selective gas-permeable membrane comprises 32~49% by weight of a polymer matrix, 1.0~4.5% by weight of an ion selective material, 50~66% by weight of a plasticizer, and 0~1.5% by weight of a lipophilic additive.

6. The microchip-based differential oxygen gas sensor as set forth in claim 5, wherein the polymer matrix composes of a mixture of poly (vinyl chloride) and polyurethane by weight proportions of 90:10~10:90.

7. The microchip-based differential oxygen gas sensor as set forth in claim 5, wherein the plasticizer is selected from the group consisting of bis(2-ethylhexyl) sebacate, bis(2-ethylhexyl) adipate, 2-nitrophenyl octyl ether, and mixture thereof.

8. The microchip-based differential oxygen gas sensor as set forth in claim 5, wherein the lipophilic additive is selected from the group consisting of potassium tetrakis(4-chlorophenyl)borate, sodium tetrakis[3,5-bis(trifluoromethyl)phenyl]borate, sodium tetraphenylborate, tetradodecylammonium tetrakis(4-chlorophenyl)borate, and mixture thereof.

9. The microchip-based differential oxygen gas sensor as set forth in claim 5, wherein the ion-selective gas-permeable membrane further comprises 0–4.0% by weight of a silicon-based adhesive.

10. The microchip-based differential oxygen gas sensor as set forth in claim 9, wherein the silicon-based adhesive is selected from the group consisting of N-[3-(trimethoxysilyl) propyl]ethylene diamine, 3-(trimethoxysilyl)propyl methacrylate, and 3-glycidoxypropyltrimethoxy silane.

11. A microchip-based potentiometric multi-sensor capable of detecting two or more ions and gas species at the same time comprising
   a) an alumina substrate 5;
   b) an electrode unit I comprising Ag/AgCl electrode 12 on a Ag—pt layer 11; a hydrogel layer 21, placed on the Ag/AgCl electrode 12; and an aromatic polyurethane membrane 22, deposited over the hydrogel layer 21, wherein the aromatic polyurethane membrane 22 is an outer membrane of a insulating film 6,
   c) an electrode unit II comprising Ag/AgCl electrode 12 on a Ag—Pt layer 11; a buffered hydrogel layer 14, placed on the Ag/AgCl electrode 12; and hydrogen ion selective membrane 15, placed top the buffered hydrogel layer 14, which hydrogen ion selective membrane 15 is enclosed within a well formed by the insulating film 6,
   d) an electrode unit III comprising Ag/AgCl electrode 12 on a Ag—pt layer 11; a unbuffered hydrogel layer 31, placed on the Ag/AgCl electrode 12; and hydrogen ion selective membrane 15, deposited over the unbuffered hydrogel layer 31, which hydrogen ion selective membrane 15 is enclosed within the well formed by the insulating film 6,
   e) an electrode unit IV comprising a cobalt-plated electrode layer 13 on a Ag—Pt layer 11; a buffered hydrogel layer 14, placed on the Ag/AgCl electrode 12; and a hydrogen ion selective membrane 15, deposited over the buffered hydrogel layer 14, which hydrogen ion selective membrane 15 is enclosed within the well formed by the insulating film 6, and
   f) an electrode unit V comprises Ag/AgCl electrode 12 on a Ag—Pt layer 11; a potassium ion selective membrane 41 deposited over the Ag/AgCl electrode 12, which potassium ion selective membrane 41 is enclosed within the well formed by the insulating film 6,
   whereby said insulating film 6 is deposited over the entire aluminum substrate 5, except for the areas of the electrodes so as to insulate the electrode units I~V.

12. The microchip-based potentiometric multi-sensor as set forth in claim 11, wherein the electrode unit IV as a working electrode and the electrode unit II as a reference electrode constitute an oxygen gas sensor.

13. The microchip-based potentiometric multi-sensor as set forth in claim 11, wherein the electrode unit II as a working electrode and the electrode unit I as a reference electrode constitute a hydrogen ion sensor.

14. The microchip-based potentiometric multi-sensor as set forth in claim 11, wherein the electrode unit III as a working electrode and the electrode unit II as a reference electrode constitute a carbon dioxide sensor.

15. The microchip-based potentiometric multi-sensor as set forth in claim 11, wherein the electrode unit V as a working electrode and the electrode unit I as a reference electrode constitute a potassium ion sensor.

16. The microchip-based potentiometric multi-sensor as set forth in claim 11, wherein the hydrogel layer 21 is selected from the group consisting of 0.2 M EPPS (N-(2-hydroxyethyl)piperazine-N'-(3-propanesulfonic acid))-NaOH pH 7.9; 0.2 M MES (2-(morpholino)ethanesulfonic acid)-NaOH, pH 5.5; and 0.2 M KHP (potassium hydrogen phthalate)-NaOH, pH 4.0.

17. The microchip-based potentiometric multi-sensor as set forth in claim 11, wherein the unbuffered hydrogel layer 31 is a hydrogel comprising $2.4 \times 10^{-2}$~$8.1 \times 10^{-2}$% by weight (3~10 mM) of sodium bicarbonate, $5.6 \times 10^{-4}$~$5.6 \times 10^{-3}$% by weight (0.1~1.0 mM) of sodium chloride or potassium chloride and 1~4% by weight of a hygroscopic material, and carbonic anhydrase in an amount of 0.1~6.0 mg per ml of the hydrogel.

* * * * *

UNITED STATES PATENT AND TRADEMARK OFFICE
CERTIFICATE OF CORRECTION

PATENT NO. : 6,663,756 B2
DATED : December 16, 2003
INVENTOR(S) : Lee et al.

It is certified that error appears in the above-identified patent and that said Letters Patent is hereby corrected as shown below:

Column 13,
Line 49, "placed top" should be corrected to -- placed on top --.

Column 14,
Line 29, "Ag-pt" should be corrected to -- Ag-Pt --.
Line 37, "placed top" should be corrected to -- place on top of the --.
Line 42, "Ag-pt" should be corrected to -- Ag-Pt --.

Signed and Sealed this

Tenth Day of August, 2004

JON W. DUDAS
*Acting Director of the United States Patent and Trademark Office*